United States Patent
Himmelhaus et al.

(10) Patent No.: US 6,756,014 B2
(45) Date of Patent: Jun. 29, 2004

(54) BIOCHEMICAL SENSOR AND BIOCHEMICAL TESTING SYSTEM USING THE SAME

(75) Inventors: Michael Himmelhaus, Karlsruhe (DE); Kenko Uchida, Tokyo (JP); Hiroyuki Takei, Hatoyama (JP)

(73) Assignee: Hitachi, Ltd., Tokyo (JP)

( * ) Notice: Subject to any disclaimer, the term of this patent is extended or adjusted under 35 U.S.C. 154(b) by 125 days.

(21) Appl. No.: 10/022,735

(22) Filed: Dec. 20, 2001

(65) Prior Publication Data

US 2002/0123155 A1 Sep. 5, 2002

(30) Foreign Application Priority Data

Mar. 2, 2001 (JP) ........................................ 2001-057642

(51) Int. Cl.[7] .............................................. G01N 33/48
(52) U.S. Cl. ....................... 422/61; 436/525; 436/164; 436/174; 436/178; 435/174
(58) Field of Search ............................. 436/94, 91, 164, 436/174, 178, 501, 518, 525; 422/61; 435/174

(56) References Cited

FOREIGN PATENT DOCUMENTS

| EP | 0 798 561 A1 | 10/1996 |
| EP | 1 139 100 A2 | 3/2001 |
| EP | 1 139 100 A3 | 3/2001 |
| JP | 11-243997 | 3/1998 |
| JP | 2000-055920 | 8/1998 |
| WO | WO 90/01564 | 8/1989 |
| WO | WO 98/09153 | 8/1997 |
| WO | WO 01/23459 A1 | 9/2000 |
| WO | WO 01/23888 A1 | 9/2000 |

OTHER PUBLICATIONS

Stephen P.A. Fodor, J. Leighton Read, Micahel C. Pirrung, Lubert Stryer, Amy Tsai Lu and Dnnis Solas, "Light–Directed, Spatially Addressable Parallel Chemical Synthesis," Science, vol. 251 (Feb. 15, 1991), pp. 767–773.

Mark Schena, Dan Shalon, Ronald W. Davis and Patrick O. Brown, "Quantitative Monitoring of Gene Expression Patterns with a Complementary DNA Microarry," Science, vol. 270, Oct. 20, 1995, pp. 467–470.

(List continued on next page.)

*Primary Examiner*—Lyle A. Alexander
(74) *Attorney, Agent, or Firm*—Reed Smith LLP; Stanley P. Fisher, Esq.; Juan Carlos A. Marquez, Esq.

(57) ABSTRACT

The invention provides a biochemical sensor with probes uniformly caught in each section. The probes used for detecting a substance of interest are caught in advance on particles, and the particles are fixed in each of sections arranged in form of lattice using a chemical patterning method on the surface of a baseplate. In each section, the particles attached with probes caught on the surface are fixed in single layer and tightly packed. The quantity of the particles fixed on the baseplate is determined by using a light scattering from the particles or by labeling the particles in advance with fluorescent substance. Therefore, the number of probes caught in each section of individual biochemical sensor is determined so as to allow the substance of interest to be detected with high accuracy.

9 Claims, 7 Drawing Sheets

OTHER PUBLICATIONS

Claire E. Jordan, Anthony G. Frutos, Andrew J. Thiel and Robert M. Corn, "Surface Plasmon Resonance Imaging Measurements of DNA Hybridization Adsorption and Streptavidin/DNA Multilayer Formation at Chemically Modified Gold Surfaces," Analytical Chemistry, vol. 69, No. 24, Dec. 15, 1997, pp. 4939–4947.

Joseph Sambrook, "Isolation of RNAs," Molecular Cloning (1989), pp. 7.6–7.9.

Jing Cheng, Edward L. Sheldon, LeiWu, Adam Uride, Louis O. Gerrue, John Carrino, Michael J. Heller and James P. O'Connell, "Preparation and hybridization analysis of DNA/RNA from E. coli on microfabricated bioelectronic chips," Nature Biotechnology, vol. 16 (Jun. 1998), pp. 541–546.

BIOCHEMICAL SENSOR AND BIOCHEMICAL TESTING SYSTEM USING THE SAME

BACKGROUND OF THE INVENTION

1. Field of the Invention

The present invention relates to a biochemical sensor chip for simultaneously testing a plurality of biochemical specimens so as to find out whether a substance of interest, such as antibody, antigen, single-stranded DNA, receptor, ligand, enzyme, etc., is present. In particular, the invention relates to a DNA chip and a biochemical sensor chip called a DNA array.

2. Description of Related Art

As the biochemical sensor chip, a DNA chip is known for detecting a plurality of the substances of interest at the same time. This DNA chip is a biochemical sensor chip where a plurality of different DNAs are fixed as probes on a baseplate, such as glass. The probe as mentioned here is a molecule or a substance, which specifically identifies a molecule of interest.

The following methods are known for preparing a DNA chip: A first method by synthesizing DNA probes on a baseplate (Prior Art 1: Science, Vol.251, pp.767–773 (1991)), and a second method by spotting DNA probes already synthesized sequentially (one by one) on a baseplate (Prior Art 2: Science, Vol.270, pp.467–470 (1995)).

According to the first method, on a baseplate made of such as silicon, glass, etc., different types of DNAs of several tens mer are synthesized and founded in one of a plurality of regions by photo-lithography and the technique of photochemical reaction. For instance, a first type of DNA is bonded in a first region, and a second type of DNA is bonded in a second region.

To detect a substance of interest, to-be-tested genes are digested to several tens mer to obtain short fragments. Each fragment is labeled with a fluorescent dye to be added to the surface of the DNA chip. If a DNA fragment (e.g. a cDNA fragment) in complementary relation with the DNA synthesized on the DNA chip is present in the specimen, this DNA fragment is hybridized with the respective DNA on the DNA chip.

After washing off the other DNA fragments, which are not hybridized with the respective DNA on the DNA chip, the DNA chip is examined by an optical detection method with a high sensitivity, such as using a confocal microscopy, and fluorescence signals from the fluorescent dye labeling the DNA fragment in a specific region of the DNA chip are detected. The DNAs bonded in each region of the DNA chip is already known, and the DNA fragment is identified from fluorescence signals detected from each region of the DNA chip.

The second method is a method by spotting DNA probes one by one to each section. In order to facilitate adsorption of DNA, the surface of the baseplate made of such as glass, silicon, polymer material, etc. is coated with a material such as polylysine. Then, a very small quantity of DNA solution is dropped onto the baseplate using a micro-pipette, a syringe, etc. to be dried. As a result, a plurality of spots of DNA probes different from each other are formed on the baseplate. The DNA probes fixed in each of the sections are brought into reaction with to-be-tested genes and modified with the fluorescent substance as described above. Any reacted genes are detected by using any commercially available confocal microscopes or DNA micro-array scanners.

Prior art 3 (JP-A-11-243997) discloses a method by identifying the types of probes attached to the particles based on shape or size of the particle, dielectric property, or color. Light is irradiated on a probe array where the specimen and the particles with reacted probes are arranged two dimensionally. Any signal detected from the passing light through a transparent stage of the probe array by a CCD camera are inputted to a data processing system. After confirming that the particles are not overlapping, the shape of particles (beads) are determined.

Prior art 4 (JP-A-2000-055920) provides a method by arranging polymer microspheres or metal particles already modified with biomolecules, such as DNA, antigen, antibody, receptor, ligand, enzyme, etc. on a baseplate. A baseplate with a gold thin film deposited on the surface is prepared. A template with a plurality of partitions is placed on the baseplate. Then, polystyrene particles suspended in a carbodiimide solution with concentration of 1–50 mM is poured into each of the partitions. Thus, a baseplate is prepared where one layer of different polystyrene particles is adsorbed on each region.

In the DNA chip as described in the prior art, there is problem in uniformity of the capture of probes formed or fixed on the baseplate. Specifically, in each of the methods described in the prior art 1 or 2, the adsorption of the molecules is not always uniform. It is difficult to confirm the adsorbing condition of the molecules by any non-destructive means, and it is almost impossible to determine and evaluate the uniformity of the probes formed or fixed on the baseplate.

The DNA probes on the DNA chip are brought into reaction with the substance of interest, and the substance bonded with DNA probes on the DNA chip is detected. In these processes, no method is known to estimate the number of DNA probes on the baseplate dropped off from the DNA chip. As a result, there is problem in that the intensity of the signal detected from each region of the DNA chip does not accurately reflect the quantity of the substance present in the specimen.

Further, probes are fixed in small regions with a small surface area. As a result, there is problem that the probes cannot be fixed in a quantity necessary to provide a signal with sufficient intensity.

SUMMARY OF THE INVENTION

It is an object of the present invention to provide a biochemical sensor for determining number of particles attached (with probes caught on the surface) uniformly fixed in each section and for increasing surface area of the regions to improve sensitivity.

According to the biochemical sensor of the present invention, particles attached with probes for detecting a substance of interest are adsorbed and fixed in each of the sections, which are arranged in a lattice/grid on a baseplate by a chemical patterning method. The particles attached with probes caught in each of the sections are fixed in one single layer and in a very tightly packed state. On the particles fixed in each section, different types of probes are caught. A specimen solution containing the substances of interest labeled with fluorescent substance is poured onto the surface of the baseplate. The substances of interest react and bond to the probes at any sections. By washing the surface of baseplate, un-reacted substances contained in the specimen solution are removed and the substances bonded to the probes attached to the surface of the particles are remained on the baseplate. Different types of the substances of interest labeled with fluorescent substance and bonded to the probes are detected in each section by optically applying a commercially available well-known apparatus for detecting fluorescence emitted from the fluorescent substance excited by irradiation of laser light. Because the particles are fixed in each of sections, apparent surface area per unit area in each section is increased.

Alternatively, one type of substances of interest is served at different densities in each section. There are at least two approaches to attach baseplate sections with different densities of the same kind of substances. One approach is to attach different densities of particles with substantially the same number of probes to the sections. Another approach is to attach the same density of particles each of which has different number of probes to the sections.

The particles attached with probes caught on the surface are prepared in large quantity in advance in a reaction container. Approximately the same number of probes are uniformly caught on each of the particles.

According to the biochemical sensor of the present invention, number of particles fixed in each section on the baseplate is determined by light scattering from the particles. Or, by measuring fluorescent light from fluorescence label of the particles which are labeled in advance, the number of probes in each section can be determined. In each of the processes where the biochemical sensor is used, the quality of the probes in each section of the biochemical sensor is assured, and the substance of interest is detected with high accuracy.

The biochemical sensor of the present invention comprises a plurality of particles attached with approximately the same number of probes each selectively bonding with a substance of interest in a specimen The probes are caught on the surface of the particles, and a planar baseplate has a plurality of sections arranged separately from each other. The particles are fixed so that the number of the particles per unit area in each of the sections is approximately the same, and one layer of the particles is fixed on each of the sections.

The method for manufacturing a biochemical sensor according to the present invention comprises preparing a plurality of particles attached with approximately the same number of probes bonding with the substance of interest in the specimen, having said probes caught on the surface of said particles, and having said particles prepared in different containers for each type of said probes, and having a plurality of section arranged separately from each other on a planar baseplate. The method further comprises fixing a plurality of particles with different types of probes caught on the surface of the particles such that the number of the particles per unit area in each of the sections is approximately the same, or fixing one layer of particles where different types of probes are caught. The method is also characterized in that the number of the particles fixed per unit area in each of the sections is non-destructively determined by irradiating light to regions in each of the sections where the particles are fixed.

Different substances of the same type, such as DNAs, RNAs, proteins, etc., are extracted from different sources, such as different patients. For detecting different types of substances, such as DNAs, RNAs, proteins, etc., different baseplates are used, i.e., one baseplate for detecting one type of substances. For example, if a DNA is used as a probe, all of the probes fixed on a baseplate through particles are DNAs. It is not suggested to mix probes of different types on a single baseplate.

There is no description regarding the above features in any of the prior art references. A typical example of the probe in the present invention is a single-stranded DNA, and typical examples of the particles include polymer particles (such as polystyrene particles) and glass particles.

In the above description, the expression that "the particles attached with substantially the same number of probes on the surface" are defined as follows. It is assumed that the number of probes caught on the surface of the particles (i=1, 2, . . . , N) is $X_i = X_1, X_2, \ldots, X_N$ respectively, and that average value of $X_i = X_1, X_2, \ldots, X_N$ is $X_{av}$. Then, at statistical probability of 95%, number of probes 50% above or below the average value $X_{av}$ (i.e. number of probes within the range of $0.5\ X_{av}$–$1.5\ X_{av}$) are caught on the particles. Specifically, if number of probes $X_i$ caught on the particles "i" is within the range of $0.5\ X_{av}$–$1.5\ X_{av}$, the particles "i" can be regarded as the particles attached with approximately the same number of probes on the surface.

Also, in the above description, the expression that "number of particles per unit area in each of the sections, i.e. density, is substantially the same" is defined as follows: It is assumed that the number of particles per unit area fixed in sections (i=1, 2, . . . , M) is $Y_i = Y_1, Y_2, \ldots, Y_M$ respectively, and that average value of $Y_i = Y_1, Y_2, \ldots, Y_M$ is $Y_{av}$. Then, at statistical probability of 95%, it is defined as where the number of the particles falls 50% above or below the average value $Y_{av}$ (i.e. number of the particles in the range of $0.5\ Y_{av}$–$1.5\ Y_{av}$) as "substantially the same". That is, if the number $Y_i$ of the particles fixed in the section "i" is within the range of $0.5\ Y_{av}$–$1.5\ Y_{av}$, the section "i" can be regarded as a section with substantially the same number of particles fixed.

Other and further objects, features and advantages of the invention will appear more fully from the following description.

BRIEF DESCRIPTION OF THE DRAWINGS

The preferred embodiments of the present invention are illustrated in the accompanying drawings in which.

DETAILED DESCRIPTION OF THE PREFERRED EMBODIMENTS

Figure 1A:
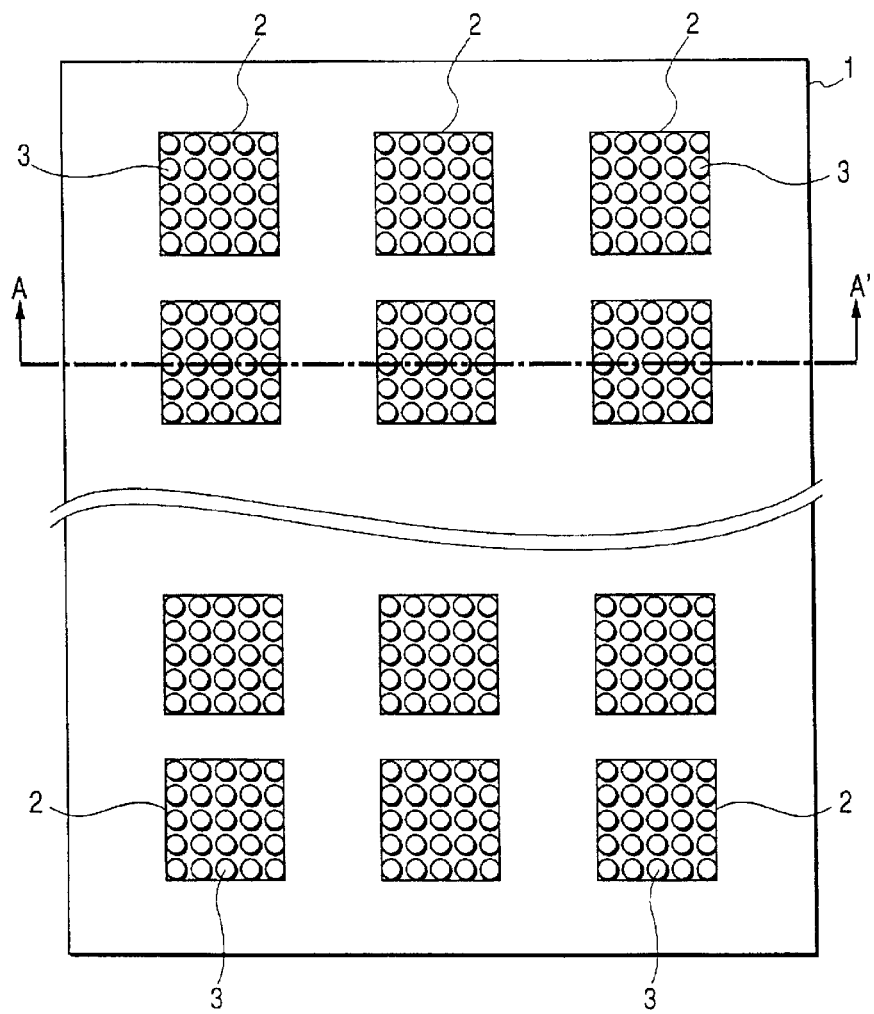
FIGS. 1(A) and 1(B) show an arrangement of a biochemical sensor of a first embodiment of the present invention.

In the embodiments of the present invention, before or after the manufacture of the biochemical sensor, a plurality of particles attached with approximately the same number of probes each selectively bonding with the substance of interest in the specimen are prepared in large quantity in containers with different types of probes.

In the biochemical sensor of the embodiment of the present invention, a region of deposition film of a metal other than gold is arranged in a lattice/grid on the surface of a planar baseplate. Next, a gold deposition film is formed over the whole surface of the baseplate including the region of the metal deposition film. Then, in a region where the metal deposition film and the gold deposition film are not overlapped or in a region where the metal deposition film and the gold deposition film are overlapped on each other, a plurality of sections separated from each are provided. In each of these sections, a plurality of particles are fixed, which have as many probes as those selectively bonded with the substance of interest in the specimen. The number of the particles fixed per unit area in each section is determined by a non-destructive method, ex. by irradiating light to each section.

When the metal deposition film is formed with one of Ti, Cu, and Co, a plurality of sections are formed in the region where the gold deposition film and the metal deposition film are not overlapped. When the metal deposition film is formed with Ag or Cr, a plurality of section are formed in a region where the gold deposition film and the metal deposition film are overlapped.

The plurality of particles are fixed in such manner that the number of the particles per unit area in each section is substantially equal to each other, and a plurality of the particles are fixed on each section in one layer. When polystyrene particles are used as the particles, polystyrene particles are fixed in each section on the surface of the baseplate by thermal welding.

The substances of interest as detected by the biochemical sensor of the present invention include antibody, antigen, single-stranded DNA, receptor, ligand, enzyme, etc. In the following description, a single-stranded DNA is taken as an example of the substance of interest. A substance-probe combination could be DNA-DNA, antibody-antigen, receptor-ligand, enzyme-ligand, DNA-Protein, DNA-RNA, etc. Description will be given below referring to the drawings.

1st Embodiment

In the first embodiment, description is given on the procedure for manufacturing the biochemical sensor (DNA micro-array) with a DNA serving as a probe (DNA probe), and for simultaneously detecting a plurality of expressed genes with the biochemical sensor. Specifically, the particles attached with DNA probes caught on the surface are fixed in each of a plurality of sections arranged in a lattice on the baseplate. After pouring a solution containing cDNAs prepared from a biological specimen onto the surface of the baseplate, by hybridizing the cDNAs with DNA probes caught on the particles fixed in each section, expressed genes are detected.

In general, when a plurality of expressed genes are detected at the same time, a sensor called a DNA chip or a DNA micro-array is generally used. In this sensor, the DNA serving as the probe is fixed on a baseplate, such as nylon film, slide glass, silicon, etc. From mRNAs purified from a biological specimen, cDNAs labeled with fluorescent substance are synthesized. Then, expressed genes are determined by hybridizing DNA probes on the baseplate and cDNAs. (See Prior Art 5; Protein Nucleic Acid Enzyme, Vol.43, No.13, pp.2004–2011 (1998); "DNA Chip Technique and Its Application".)

Figure 1B:
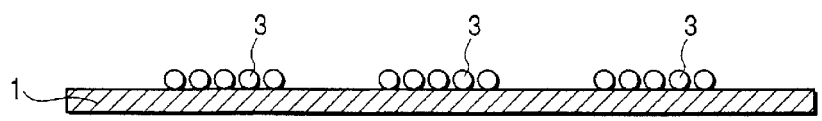

FIG. 1 shows an arrangement of a biochemical sensor of the first embodiment of the present invention. FIG. 1(A) is a plane view of the biochemical sensor, and FIG. 1(B) is a cross-sectional view taken along the line A–A'. As shown in FIG. 1, particles 3 with DNA probes caught on the surface are fixed in each of a plurality of sections 2 provided in a lattice on a baseplate 1 made of a material, such as slide glass, glass, silicon, polymer material, etc. In the example shown in FIG. 1, a rectangular baseplate 1 is used, while a square baseplate may be used.

In each of the sections 2, the particles 3 are attached with different types of DNA probes on the surface. In all of the sections 2 shown in FIG. 1A, the particles 3 with the same type of DNA probes caught on the surface may be fixed, or the particles 3 with an i-th type of DNA probes caught on the surface may be fixed on an i-th section shown in FIG. 1A (where i=1, 2, . . . , N).

As the baseplate 1 shown in FIG. 1, a slide glass of 76 mm by 26 mm and 0.9 mm thick and made of transparent quartz is used, for instance. In FIG. 1, a small number of square sections 2 are shown. Each of the sections 2 is in square or rectangular shape with a side of 20–200 µm in length, or a circular shape with a diameter of 20–200 µm. The distance between each of the sections is set at 20–200 µm.

Polystyrene particles each in spherical shape and 5 nm–100 µm in diameter may be used as the particles 3. It is preferable to use polystyrene particles each of 50–200 nm in diameter because the particles are more conveniently maintained on the surface of each section. On each of the polystyrene particles 3, DNA probes of about 400–6000 molecules are caught.

It is assumed that one side of a square section 2 is "d", and the radius of the spherical particle 3 is "r". It is also assumed that the particles 3 are arranged in a square lattice on the surface of the section 2, and that concentration of DNA probes caught on the surface of the particles 3 is "n" molecules/cm$^2$. In this case, $(d/(2r))^2$ particles 3 are fixed in the section 2. In total, DNA probes of $(d/(2r))^2 \times 4\pi r^2 n = \pi d^2 n$ molecules are caught in the section 2.

In contrast, if DNA probes are fixed directly on the section 2 at the same concentration ("n" molecules/cm$^2$), only DNA probes of $d^2 n$ molecules are fixed in the section 2. Therefore, when the particles 3 with DNA probes caught on the surface are fixed in the section 2, compared with the case where DNA probes are directly fixed in the section 2, π times as many DNA probe molecules are caught in the section 2.

Here, it is assumed that a slide glass of 76×26 mm and 0.9 mm thick is used as the baseplate 1, and a range of 20×50 mm in size on the baseplate is used for the sections. It is also assumed that the section 2 is a square with a side of 100 µm long and the distance between the sections is 100 µm long, and that polystyrene particles have a spherical diameter of 100 nm. 25,000 sections are formed on the slide glass, and about 10$^6$ of polystyrene particles 3 are caught in each of the sections 2. Specifically, on the surface of each of the sections 2, 10$^6$ polystyrene particles 3 are fixed at a concentration of 1010 particles/cm$^2$.

Here, it is assumed that average number of molecules of DNA probes caught on each of the polystyrene particles 3 is about 1,600 molecules. Then, about 1.6×10$^9$ molecules of DNA probes are caught in each of the sections 2.

Figure 2:
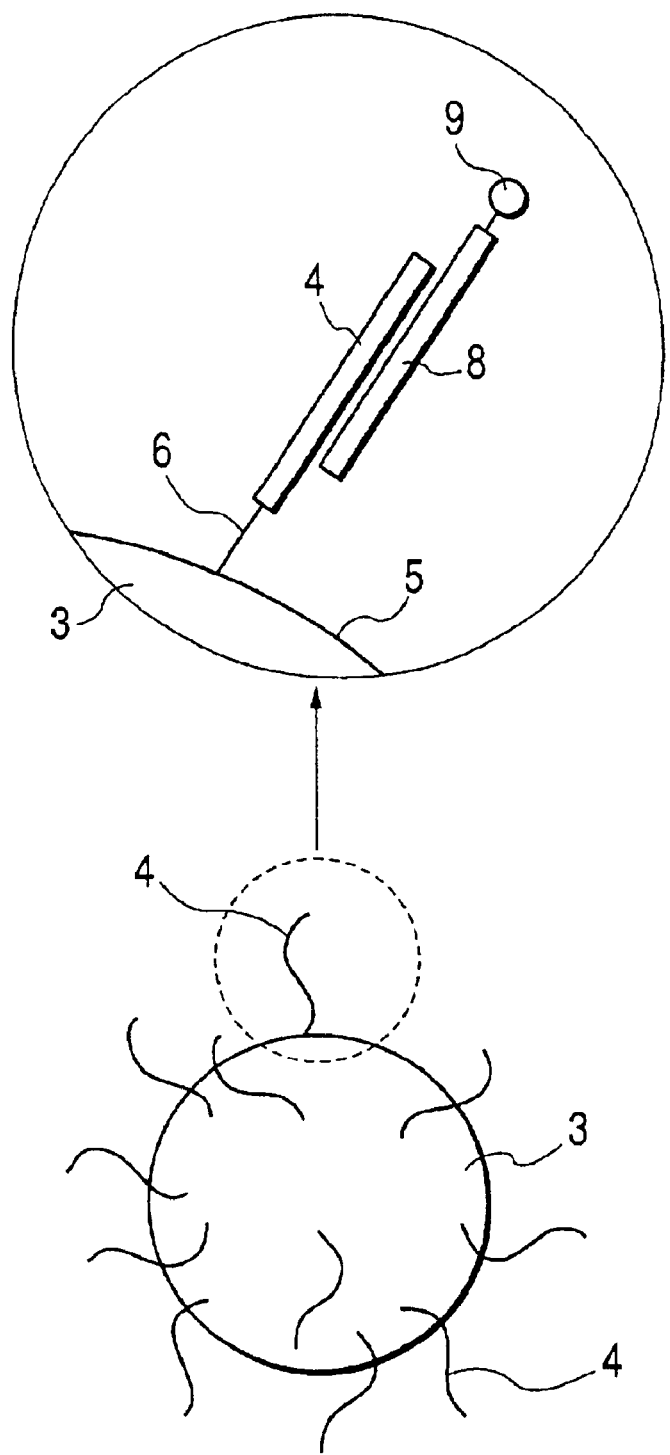
FIG. 2 shows particles where DNA probes are caught of the first embodiment of the present invention and the reaction between the DNA probes and the substance of interest.

FIG. 2 is partially enlarged view to show the reaction of the particles attached with DNA probes of the first embodiment and the reaction of DNA probes with the substance of interest. As shown in the partially enlarged view of a circular portion (at the top of FIG. 2) shown by dotted line at the bottom of FIG. 2, the particles 3 attached with DNA probes are prepared. Modification, such as sylylenization or silanization, is performed such that a covalent bond or a hydrogen bond with the DNA may easily occur on the surface 5 of the particle.

Now, description is given on synthesis of the DNA probes. An amino group added with linkers is introduced to 5' terminal of a primer on the sense side to cover the DNA region, which serves as a probe, and a normal primer is used on the antisense side. These primers and template DNAs including the regions, which serve as probes, are used to perform PCR amplification. The amplified DNA is purified with a commercially available purification kit of a PCR amplification fragment (e.g. purification kit manufactured by QUIGEN), and the DNA content in the amplified DNA is quantitatively determined from absorbance of light with a wavelength of 260 nm.

Commercially available particles with surface modification are used as the particles serving as carriers to catch DNA probes. For instance, when particles with active aldehyde group on the surface (Polybead Polyacrolein Microspheres made by Polyscience Inc., distributed in Japan by Funakoshi) are used, DNA probes with amino groups introduced to terminals are bonded. On the contrary, when the particles having amino groups on the surface are used, DNA probes modified with aldehyde groups on terminals are used.

Description is given below on the procedure for DNA probes with amino group at the terminals being caught on the particles with active aldehyde groups on the surface. The particles are suspended in "3× SSC" solution (where "1× SSC" means mixed solution containing NaCl (0.15 M), trisodium citrate (15 mM; pH 7.0); "3× SSC" is a solution with 3 times as high concentration of the compounds as "1× SSC") Then, the concentration of DNA probes is 0.5 mg/ml. The particles are rinsed with 0.2% SDS and then washed with distilled water by three times. The particles are suspended in a solution of sodium borohydride (a solution prepared by dissolving 1 g of sodium boron hydride into 300 mL of phosphate buffer and 100 mL of ethanol), and the solution is left to stand for 5 minutes. Then, the particles are immersed in distilled water at 95° C. for 2 minutes. Again, the particles are suspended in 0.2% SDS solution and the solution is left for one minute. After the particles are washed with distilled water three times, the particles are dried and stored in a cold and dark place.

As the methods for catching DNA probes on the surface of the particles, there are other methods already known, such as using biotin and avidin, utilizing a reaction of gold and SH group (Prior Art 6: Analytical Chemistry, Vol. 69, pp.4939–4947 (1997)). All of these methods can be used in the first embodiment of the present invention. When the reaction of gold and SH group is used, gold should be coated in advance on the surface of the particles.

As shown in FIG. 2, DNA probes 4 are caught on the surface 5 of the particles via a linker 6 to catch DNA probes. A substance of interest 8 bonded with a labeling substance 9 is bonded to the DNA probe 4 by a complementary strand bond. As the labeling substance 9, fluorescent dye of different types for each specimen is used.

In the following, description is given on a first method for attaching the particles with DNA probes on the surface of each of the sections arranged in a lattice.

FIG. 3 shows an arrangement of a biochemical sensor of the first embodiment. The particles attached with DNA probes prepared by the methods as described above are fixed in each of the sections 13 (2) arranged in a lattice as shown in FIG. 3. As it is evident from the plan view of FIG. 3(A), mask patterns 10 each in a square are coated and arranged on a baseplate 1. FIG. 3B is a cross-sectional view taken along the line A–A' in FIG. 3(A). As it is evident from the cross-sectional view of FIG. 3(C), on regions of the baseplate 1 where the mask patterns 10 are not formed, a metal other than gold is deposited in thickness of 1 nm–100 nm, and a metal thin film 12 is formed.

Next, the mask patterns 10 formed on the baseplate 1 are removed.

Figure 3A:
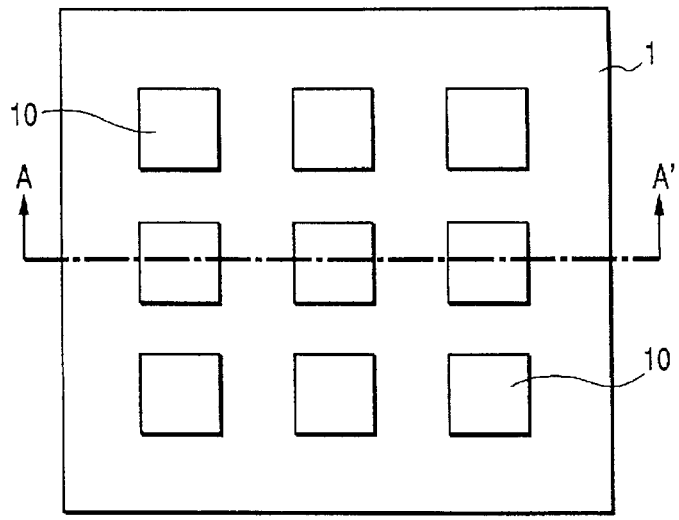
FIGS. 3(A), 3(B), 3(C), 3(D), and 3(E) show the manufacturing procedure and the arrangement of the biochemical sensor of the first embodiment of the present invention.
Figure 3B:
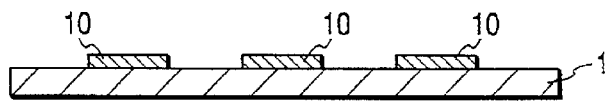
Figure 3C:
Figure 3D:
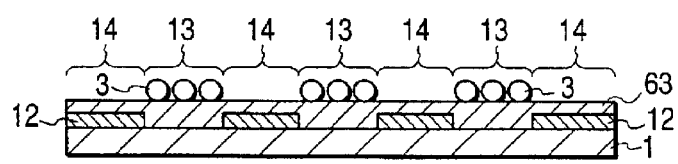

Next, as shown in the cross-sectional view of FIG. 3D, gold is deposited of 5 nm–100 nm thick. As a result, there are provided (1) gold thin film regions 13 where only metal thin films are arranged in a lattice on the baseplate 1, and (2) 2-layer film regions 14 where 2-layer films of the metal thin film 12 and the gold thin film 63 are formed.

Next, 0.1–10 mg of carbodiimide is added per 1 mL of suspension solution of particles (weight ratio: 0.1%–10%), and this mixed solution is added to the baseplate where the gold thin film regions 13 and the 2-layer film regions 14 are formed. In this case, the adding quantity of the mixed solution is 10 μL at minimum per 1 cm² of area of the baseplate. Where the mixed solution is not dried up, the mixture is set aside for one minute to one hour at room temperature, and then washed with pure water and dried.

Figure 3E:
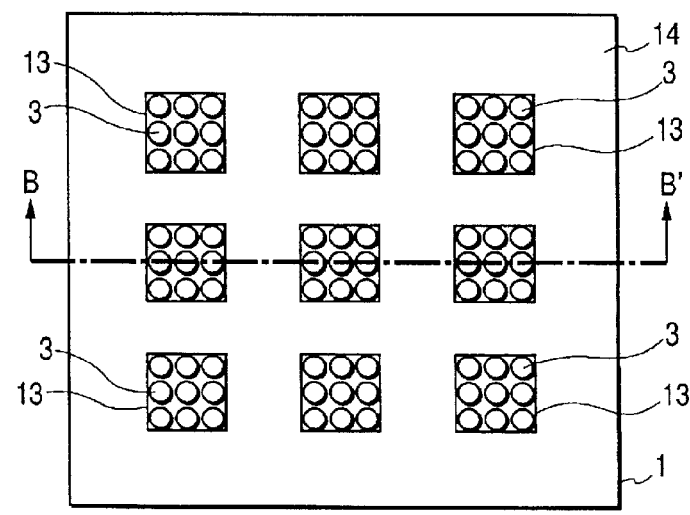

If the metal thin film 12 is made of titanium, copper, or cobalt, etc., the particles are not attached to the 2-layer film regions 14 as shown in the cross-sectional view of FIG. 3(D) (taken along the line B–B' of FIG. 3(E)) and in the plan view of FIG. 3(E), and the particles 3 are attached to the gold thin film regions 13 where only gold thin films 63 are arranged in a lattice. As a result, the sections 2 are formed where the particles 3 attached with DNA probes are fixed on the gold thin film regions 13 arranged in a lattice.

To facilitate the explanation, an example is given where 9 sections are formed on a baseplate 1 in a square in FIG. 3. The form of the baseplate 1 is not limited to square, and the number of sections is not limited to 9.

In the following, description is given on a second method for attaching the particles attached with DNA probes to each of the sections arranged in a lattice referring to FIG. 4.

FIG. 4 shows a method and an arrangement for manufacturing biochemical sensor of the first embodiment. The particles attached with DNA probes as prepared by the above method are fixed in each of sections 14 arranged in a lattice as shown in FIG. 4. As shown in the plan view of FIG. 4(A) and a cross-sectional view of FIG. 4(B), a contact mask 80 with holes 82 in a lattice on a baseplate 1, and a metal 12' other than gold is deposited of 1–100 nm thick. As shown in the cross-sectional view of FIG. 4(C), the metal thin films 12' having the same pattern as the holes 82 on the contact mask 80 are formed on the surface of the baseplate 1.

Figure 4A:
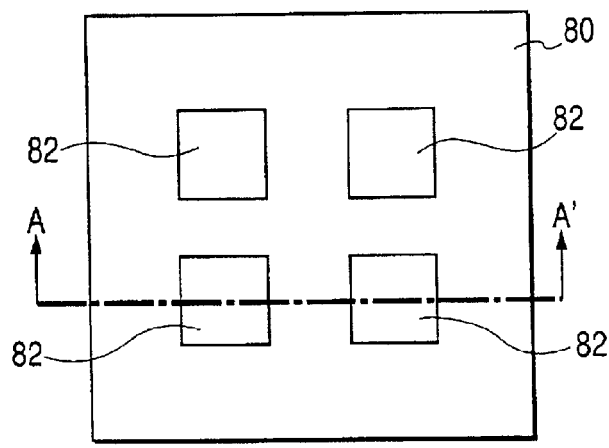
FIGS. 4(A), 4(B), 4(C), 4(D), 4(E), and 4(F) show the manufacturing procedure and another arrangement of the biochemical sensor of the first embodiment of the present invention.
Figure 4B:
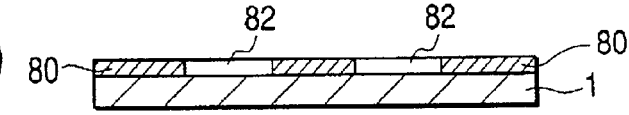
Figure 4C:
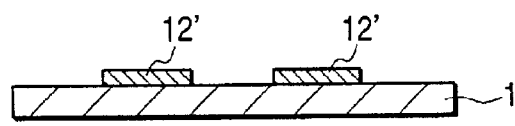
Figure 4D:
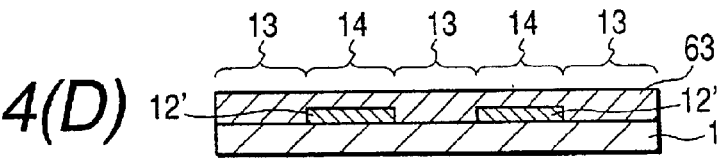

Next, as shown in the cross-sectional view of FIG. 4D, gold is deposited of 5–100 nm thick. As a result, a gold thin film region 13 with only a gold thin film 63 formed on the baseplate 1, and 2-layer film regions 14 (with metal thin films 12' and the gold thin films 63) are obtained.

Next, to a suspension solution of the particles attached with DNA probes, 0.1–10 mg of carbodiimide is added per 1 mL of the solution, and this mixed solution is added to the baseplate where the gold thin film region 13 and the 2-layer film regions 14 are formed. In this case, the adding quantity of the mixed solution is set to 10 μL at minimum per 1 cm² of the baseplate. Under the condition that the mixed solution is not dried up, the mixture is set aside for one minute to one hour at room temperature, then washed with pure water and dried.

Figure 4E:
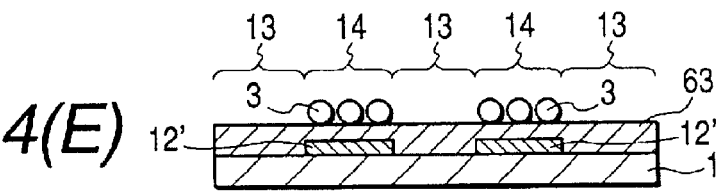
Figure 4F:
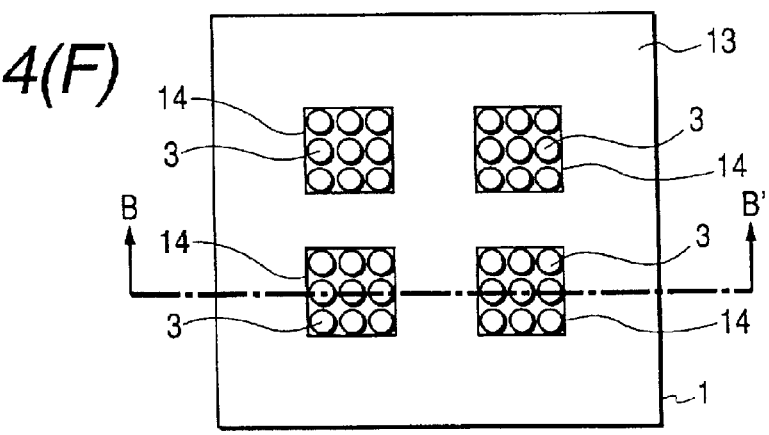

If the metal thin film 12' is silver, or chromium, etc., as shown in the cross-sectional view of FIG. 4(E) (taken along the line B–B' in FIG. 4(F)) and in the plan view of FIG. 4(F), the particles are attached to the 2-layer film regions 14 where the metal thin film 12' and the gold thin film 63 are formed in two layers, and the particles 3 are attached to the baseplate with the same patterns as the holes 82 on the contact mask 80. As a result, on the 2-layer film regions 14 arranged in a lattice, the sections 2 are formed where the particles 3 attached with DNA probes are fixed.

In FIG. 4, description is given on an example where four sections are formed on a baseplate 1 in a square. The form of the baseplate 1 is not limited to square, and the number of sections is not limited to four.

The process, in which the particles are selectively attached as explained in FIG. 3 and FIG. 4, depends upon the concentration of carbodiimide and the thickness ratio of the gold film to the metal film. As a result, it is possible to control as desired the shape of each section 2 where the particles are attached and the pattern of the sections 2.

By using the mask pattern 10 (FIG. 3(A)) in a square and coated and arranged in a lattice on the baseplate 1, or by using the contact mask 80 where the square holes 82 are arranged in a lattice (FIG. 4(A)), a plurality of sections arranged in a lattice where the particles are attached to are formed. To each section (region) where the particles are arranged in a lattice and fixed, the particles attached with different types of DNA probes are added. By performing the attaching operation, a biochemical sensor is prepared, on which DNA probes of different types are attached to each section.

Instead of the suspension solution of the DNA probes, a suspension solution of particles attached with DNA probes on the surface can be used. Using a commercially available spotter of DNA micro-array, the particles attached with DNA probes of different types on the surface can be added to each section. When the spotter is used, the particles attached with DNA probes in minimum circular shape of about 100 $\mu$m can be added to each section.

FIG. 5 shows a method for manufacturing a plurality of biochemical sensors of the first embodiment of the invention. When the probes for detecting biological substances, such as DNA, RNA, protein, etc., are attached to the particles, the reaction to catch the probes with biological substances is performed separately in container tubes 71, 72 and 73 for each different type of probes, and a large quantity of the particles in batches of the particles are prepared in advance. Typical examples of the probes for detecting biological substances are DNA probes to be hybridized with DNA molecules.

The particles attached with the probes on the surface are prepared in large quantity and in batches, and the number of molecules of the probes is approximately the same for each particle. When the particles are same, their reactivity with the probes is substantially uniform. As such, the number of probes on each particle surface is substantially same. In this case, "the particles attached with approximately the same number of molecules of probes" are defined as follows: It is assumed that the number of probes attached to the surface of the particles (i=1, 2, . . . , N) is $X_i$=$X_1$, $X_2$, . . . , $X_N$ respectively, and that average value of $X_i$=$X_1$, $X_2$, . . . , $X_N$ is $X_{av}$. Then, at statistical probability of 95%, number of probes within ±50% of the average value $X_{av}$ (i.e. number of probes within the range of 0.5 $X_{av}$–1.5 $X_{av}$) are attached to the particles. Specifically, if number of probes $X_i$ attached to the particles "i" is within the range of 0.5 $X_{av}$–1.5 $X_{av}$, the particles "i" are regarded as the particles where approximately the same number of probes are caught on the surface.

The average number of one type of probes attached to the particles is determined by using one receptive type of specimen substance of a plurality of known concentrations. The specimens with a plurality of known concentrations are first labeled with the same kind of fluorescent substance. Each specimen is then poured into a respective solution containing the particles with the same amount of probes (the number of interest). Those specimen molecules being not bonded to the probes are removed from the respective solution such that only those specimen molecules being bonded to the probes remain in the respective solution to be measured. The system then measures the intensity of fluorescence (i.e., those specimen molecules being bonded to the probes) by irradiating the specimen molecules bonded to the probes with an excitation light.

The measured intensity of fluorescence increases linearly with respect to the increase of the concentrations of the remaining specimen molecules n the respective solutions, which corresponding concentrations are known. The specific concentration of the probes is determined at a turning point from the linearly increasing fluorescence line to a plateau (a constant fluorescence level). As such, the concentration of the specimen (probes) substance is determined. If the concentration of the probes is Cn (probes/cm3), the average number probes attached to each particle is n (probes/particle), and the number of the particles contained in unit volume of the suspension solution is N (particles/cm3), n is obtained by Cn/N. Thus, n is calculated based on the above change of the fluorescence intensity originated from the fluorescent substance labeling the specimen substances bonded to the probes which are attached to the particles.

The particles of the same batch are fixed on each individual baseplate of a plurality of biochemical sensors. Description is given on more examples. The particles with 3 types of DNA probes are sequentially spotted on three or more baseplates (slide glasses).

It is assumed that DNA probes of different types are DNA probe-1, DNA probe-2, and DNA probe-3 respectively. In a reaction container 71 having a solution 21 with the DNA probe-1, DNA probe-1 is attached to the particle. In a reaction container 72 having a solution 22 with the DNA probe-2, DNA probe-2 is attached to the particle. In a reaction container 73 having a solution 23 with the DNA probe-3, DNA probe-3 is attached to the particle. By the procedure as described above, the average number of molecules in the probes for detecting biological substances attached to the particles in each reaction containers 71, 72 and 73 is obtained.

By the reactions in each of the reaction containers 71, 72 and 73, the particles with DNA probes attached to the surface are spotted sequentially on the slide glasses 24, 25 and 26 using a commercially available micro-array manufacturing system (e.g. SPBIO; manufactured by Hitachi Soft Inc.) or a pipette.

Figure 5A:
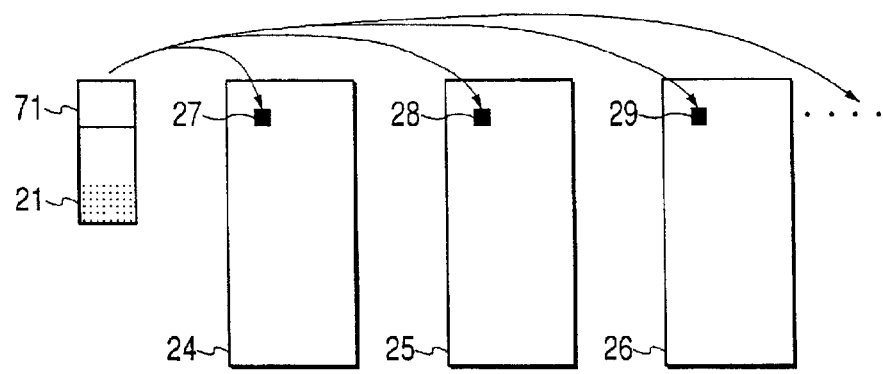
FIGS. 5(A), 5(B), 5(C) show a procedure for manufacturing a plurality of biochemical sensors of the first embodiment of the present invention.

As shown in FIG. 5(A), the suspension solution containing the particles with the DNA probe-1 caught on the surface is sequentially spotted to the slide glasses 24, 25, and 26, and spots 27, 28 and 29 are formed by the particles with the DNA probe-1 attached to the surface.

Figure 5B:
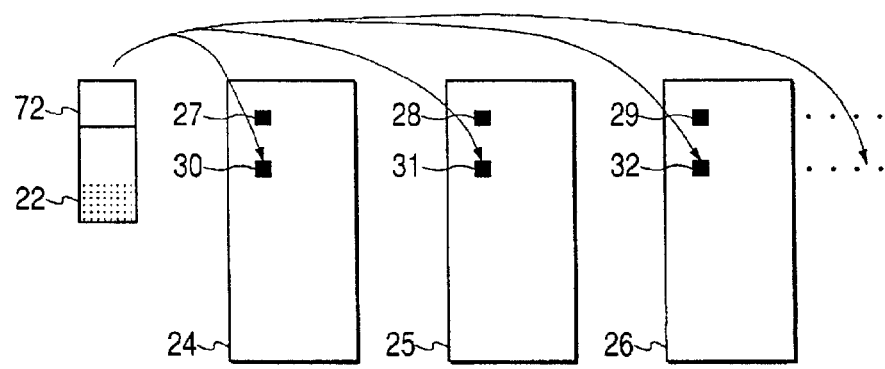

As shown in FIG. 5(B), a suspension solution containing the particles with the DNA probe-2 attached to the surface is sequentially spotted to the slide glasses 24, 25 and 26, and spots 30, 31 and 31 are formed by the particles with the DNA probe-2 attached to the surface.

Figure 5C:
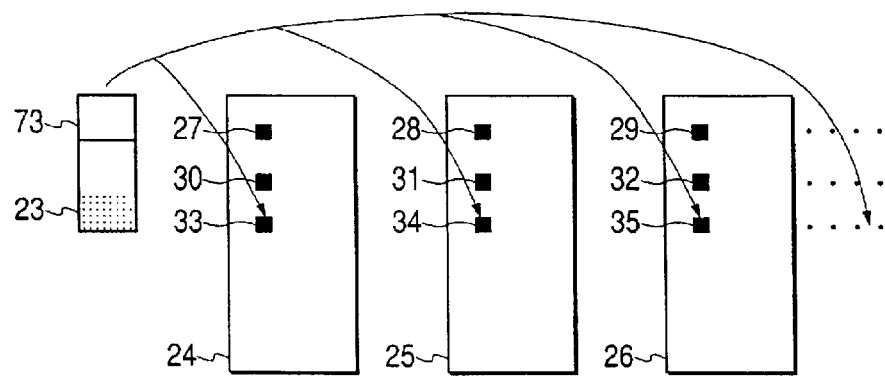

As shown in FIG. 5(C), a suspension solution containing particles with the DNA probe-3 attached to the surface is sequentially spotted to the slide glasses 24, 25 and 26, and spots 33, 34, and 35 are formed by the particles with the DNA probe-3 attached to the surface.

As described above, a large quantity of particles with DNA probes attached to the surface are prepared in the same reaction container. Then, the particles with similar reactivity are supplied to the baseplate of each of the different biochemical sensors on the slide glasses 24, 25 and 26, and the particles can be caught in each of the sections in a lattice on the baseplate of each biochemical sensor.

In FIG. 5, where the particles with 3 types of DNA probes are attached to the surface are sequentially spotted to 3 or more baseplates (slide glasses) for each different type of DNA probes. The types of DNA probes are not limited to 3 types and may be in any number of types.

Next, description is given on the preparation of RNA or DNA, which is to be tested. The molecules to be tested are amplified using dUTP labeled with fluorescent dye, such as Cy3 or Cy5, and the molecules are amplified and fluorescence-labeled.

From the cells to be analyzed, all RNAs are extracted by a known method (Prior Art 7; e.g. Molecular Cloning, second edition (Cold Spring Habor Laboratory Press (1989)), and polyA-RNA is prepared. Next, from polyA-RNA, a fluorescence-labeled cDNA is synthesized. For instance, to a mixture of 1 $\mu$g of polyA-RNA, 8 $\mu$L of superscript II (Gibco BRL) reaction buffer, 1 $\mu$g of oligo dT primer, 4 $\mu$L of 10 mM dNTP, 4 $\mu$L of dUTP labeled with Cy3 (Amersham Pharmacia; trade code PA53022) or Cy5 (Amersham Pharmacia; trade code PA 550022), and 4 $\mu$L of 0.1M DTT, is added with distilled water to make the total volume to 38 $\mu$L. After this solution is maintained at 70° C. for 10 minutes, it is quickly cooled down on ice. To the solution thus cooled, 2 $\mu$L of the superscript II (Gibco BRL) is added. After gently stirring up, the solution is maintained at 25° C. for 10 minutes, at 42° C. for 40 minutes, and at 72° C. for 10 minutes. Then, it is cooled down to room temperature. The reaction solution is condensed to 20 $\mu$L using a molecular weight cut-off filter, e.g. Microcon 30 (Millipore Corporation). Further, 400 $\mu$L of distilled water is added, and it is condensed to 10 $\mu$L. By this procedure, non-reacted dUTP and dNTP are removed. To the solution condensed to 10 $\mu$L, 4 $\mu$L of 20× SSC solution (a solution with 20 times as high concentration as that of "1× SSC"), and 6 $\mu$L of distilled water are added, and the mixture is maintained for 3 minutes in hot bath kept at 100° C. Then, it is quickly cooled on ice. To the solution thus cooled down, 200 $\mu$L of 10% SDS is added. As such, a specimen solution containing the substance of interest is prepared.

Description is given below on the reaction of the specimen solution prepared above with DNA probes attached to the particles which are fixed in each section on the baseplate of the biochemical sensor. Also, the detection of the reaction product is described. The DNA probes caught on the particles are brought into contact with the specimen solution. The biochemical sensor is placed in a sealed container, and the reaction is performed at 65° C. for 10–24 hours.

After the reaction has been completed, the baseplate of the biochemical sensor is washed for 5 minutes by 3 times with "2× SSC" solution (a solution with 2 times as high concentration as that of "1× SSC") containing 0.1% SDS. Then, it is washed for 5 minutes by 3 times with "0.2× SSC" solution, (a solution with concentration of 0.2 time of that of "1× SSC") containing 0.1% SDS. After gently rinsing with "0.2× SSC" solution, it is dried at room temperature. Next, using a commercially available scanner (e.g. ScanArray 5000; GSI Lumonics), fluorescence intensity from each spot is determined by the same procedure with a DNA microarray.

As described above, the biochemical sensor has particles with DNA probes attached to the surface and being fixed on the sections arranged in a lattice. As a result, testing and analysis of the specimens containing the substance of interest can be performed by using many types of DNA probes at one time. It is advantageous to use the methods for preparing specimens, hybridization reaction, and detecting of reaction products.

In summary, the preferred attaching sequence is as follows. The probes are first attached to the particles. Then the probe/particle combinations are fixed to the sections of the base plate. Finally, the substances of interest are attached to the probe/particle/baseplate combination. This sequence is preferred so as to selectively fixing different kinds of probes to different sections on the baseplate. Other attaching sequences, such as attaching probes to particles→attaching substances to the probe/particle combination→fixing the substance/probe/particle to different sections of the baseplate, provide different efficiency for testing plural types of substances in a specimen.

2nd Embodiment

FIG. 6 shows the second embodiment for evaluating the biochemical sensor (the first embodiment) having the particles attached with DNA probes on the surface are fixed in each of a plurality of circular sections arranged in a lattice on a baseplate. Specifically, it evaluates whether the particles fixed in each section are uniform or not, and determines the number of the particles fixed in each section. Description is given below on an example of a circular section. The shape of the section is not limited to circular shape, and it may be square or rectangular.

Figure 6A:
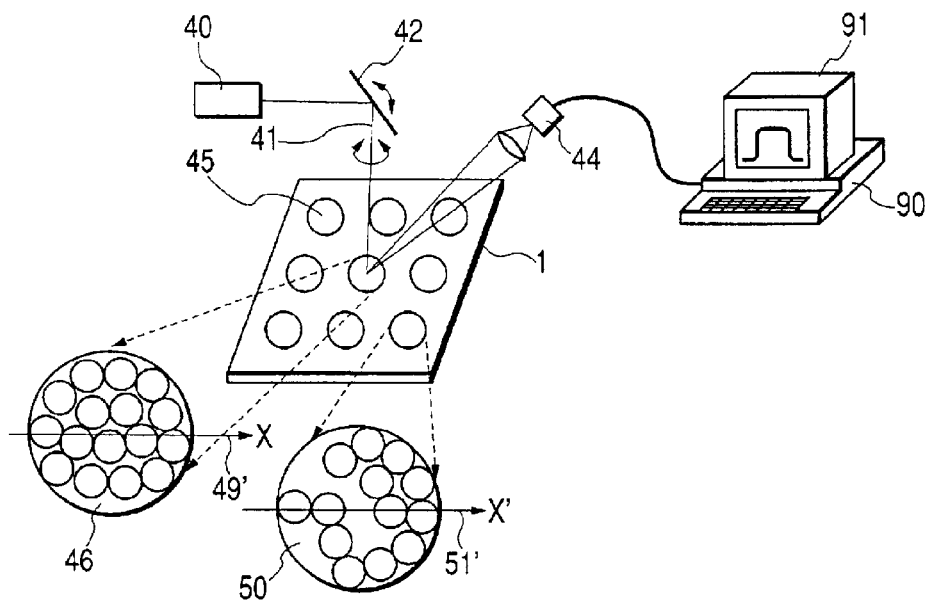
FIGS. 6(A), 6(B), 6(C), 6(D), 6(E), and 6(F) show a second embodiment of the present invention and a method for evaluating the biochemical sensor of the first embodiment.

FIG. 6(A) shows an apparatus for evaluating the degree of uniformity of particle distribution attached to the baseplate of the biochemical sensor. A laser beam 41 from a semiconductor laser 40 is irradiated to the baseplate 1 via a scanning mirror 42. Scattered light from the particles in each section on the baseplate 1 is detected by a condenser lens and a photodetector 44, arranged at a position outside of the direct reflection path. By driving the scanning mirror 42, a section 45 where the particles are attached is scanned by the laser beam 41. The output signal of the photodetector 44 is forwarded to an arithmetic unit 90 to undergo adding, averaging, smoothening, and standardizing processing. The results of the processing are displayed on a display unit 91. The laser beam is scattered at high efficiency by the particles with a size of 50 nm–100 $\mu$m, and the intensity of the scattered light depends on the concentration of the particles.

Figure 6C:
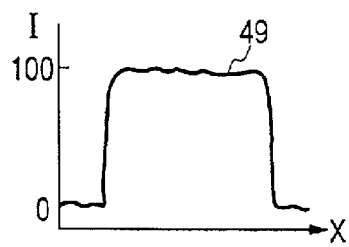
Figure 6D:
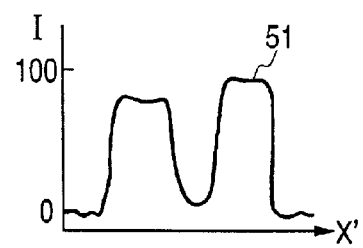
Figure 6B:
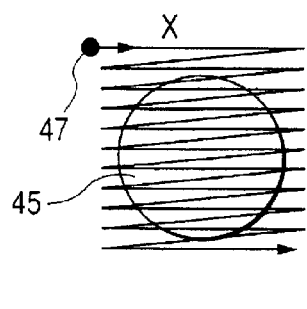

Therefore, as shown in FIG. 6(B), by irradiating a laser beam 47 to an area of less than 1/10 of the area of the region 45 where the particles are adsorbed, the region 45 is scanned 2-dimensionally in x direction and y direction (perpendicular to x direction). By monitoring the intensity of the scattering light, the degree of uniformity of particle distribution in the region 45 is evaluated.

FIG. 6(C) and FIG. 6(D) represent a drawing of the evaluation of the degree of uniformity of particle distribution in the region 45 where the particles are adsorbed. As shown in FIG. 6(C), in a region 46 where the particles are uniformly adsorbed on the baseplate, scattering light intensity 49 keeps almost constant level per the scanning of the laser beam 47 along an X direction. In contrast, as shown in FIG. 6(D), in a region 50 where the particles are not uniformly adsorbed but missed at one spot, the scattering light intensity 51 dropped at the spot per the scanning of the laser beam 47 along an X direction.

In FIG. 6(C) and FIG. 6(D), the axes of X and X' represent scanning directions of the laser beam 47 on the baseplate (i.e. the position of the laser beam in scanning directions 49' and 51' passing approximately through the center of the circular section shown in FIG. 6(A)). The y axis represents scanning light intensity (I) while the maximum value of the scattering light intensity in the region 45 is regarded as 100. To evaluate the degree of uniformity of particle distribution in the region 45, I (x, y) changes according to the scanned position (x, y), and the scattering light intensity I is determined. Then, a standardization processing is performed by regarding the maximum value of I (x, y) in the region 45 as 100. For instance, a standard deviation is taken, and if the standard deviation is lower than a predetermined value, the distribution of the particles is determined to be uniform.

Figure 6E:
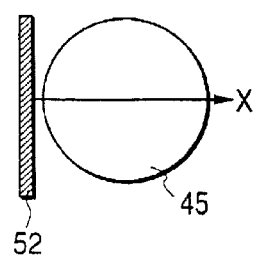
Figure 6F:
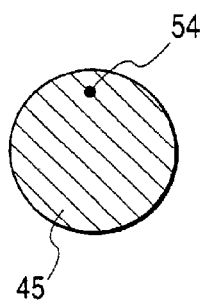

The degree of uniformity of particle distribution attached to the baseplate of the biochemical sensor can also be evaluated by irradiating a semiconductor laser beam as shown in FIG. 6(E) and FIG. 6(F). As shown in FIG. 6(E), a linear light spot 52 has a diameter corresponding to the size of the region where the particles are attached in y direction (perpendicular to x direction). This linear light spot is scanned in x direction on the region 45 where the particles are attached. Then, the light scattered from the particles is monitored. In so doing, the degree of uniformity of particle distribution in the region 45 where the particles are attached can be evaluated.

To evaluate the degree of the uniformity of particle distribution in the region 45, the I (x) changes according to the position (x) of the scattering light intensity I is determined. Then, the standardization processing is performed by regarding the maximum value of I (x) in the region 45 as 100, and a standard deviation is obtained. If the standard deviation is lower than a predetermined value, the distribution of the particles is determined to be uniform.

Also, as shown in FIG. 6(F), irradiation is performed by scanning a light 54 (shown by diagonal lines) within an area corresponding to the area of the region 45 where the particles are attached. By monitoring the scattered light intensity from the particles, the degree of uniformity of particle distribution in the region 45 where the particles are attached can be evaluated in easily and simply.

To evaluate the degree of the uniformity of particle distribution in the region 45, the scattered light intensity I in a plurality of regions 45 is determined. Then, the standardization processing is performed regarding the maximum value of I in a plurality of regions 45 as 100. Then, The distribution of the particles is determined to be uniform in the region 45 where scattered light intensity I is higher than a predetermined threshold value.

As described above, using the light scattered by the particles, the degree of the uniformity of particle distribution fixed in each section of the baseplate of the biochemical sensor is determined.

Further, the number of the particles fixed in each section on the baseplate of the biochemical sensor can be determined by the method given below.

Using a different fluorescent substance from the fluorescent substance for dyeing the substance of interest, the particles are fluorescence-labeled. Then, by detecting fluorescence intensity from the fluorescence labeled particles, the number of particles fixed in each section can be determined. For instance, by immersing polystyrene particles in 50% methanol solution containing fluorescein then drying the solution, the polystyrene particles are labeled with fluorescein.

By the method described in the first embodiment, DNA probes are attached to the particles in each section on the baseplate of the biochemical sensor. Then, as shown in FIG. 5, the particles where DNA probes are attached to the surface are spotted on the slide glass. In this case, the number of the polystyrene particles fixed in each slide glass may be varied, or the polystyrene particles may fall off in the subsequent hybridization process or washing process. However, even in such cases, the DNA probes attached to each section are brought into reaction with to-be-tested genes of interest which are dyed with fluorescent substance. Then, the fluorescence intensity of fluorescein in each section is determined at the time of defecting the reacted genes using a confocal microscope or a commercially available DNA micro-array scanner, and the number of polystyrene particles in each section on the slide glass can be determined.

By the methods as described above, the number of particles fixed in each section on the baseplate of the biochemical sensor can be determined. The average value of the number of the particles can be obtained in advance. Thus, at the time of detecting the reacted genes, it is possible to obtain the number of the DNA probes in each section.

Because the number of the DNA probes in each section of individual biochemical sensor is determined, the substance of interest is detected at high accuracy. That is, the quality of the biochemical sensor of the first embodiment can be ensured in each process where the biochemical sensor is used.

In the above, Joe (dichlorodimethoxycarboxyfluorescein), Tamra (carboxytetramethylrhodamine), or Roxis (carboxyxrhodamine) (Applied Biosystems) may be used as fluorescent substance.

3rd Embodiment

Figure 7:
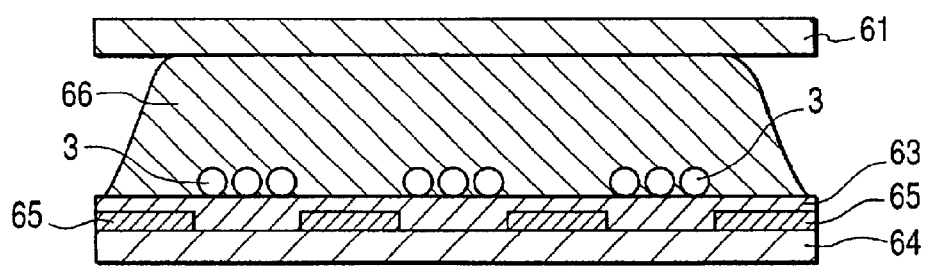
FIG. 7 is a drawing to explain a third embodiment of the invention and an arrangement of a biochemical sensor for performing hybridization with electric fields.

FIG. 7 shows the third embodiment of the invention, an arrangement of a biochemical sensor for performing hybridization with electric fields. The biochemical sensor used in the third embodiment comprises sections arranged in a lattice on the surface of the baseplate of the biochemical sensor, and the sections are defined by a deposition film of a metal other than gold and a gold deposition film arranged a of lattice on the surface of the baseplate. For example, a plurality of sections separated from each other are arranged on the planar baseplate, where the gold deposition film and the metal deposition film are not overlapped.

DNA probes selectively bonded to the substance of interest in the specimen are attached to the surface of the particles, and the particles are fixed in each section for each different type of DNA probes. The gold deposition film formed on the surface of the baseplate is used as an electrode, and the other electrode is arranged in parallel to the surface of the gold deposition film to carry out on electric hybridization reaction as described in Prior Art 8: Nature Biotechnology Vol. 16, pp.541–546 (1998).

In the third embodiment, an example is given where nucleic acid is detected by using the biochemical sensor. First, similar to the procedure for manufacturing a square sensor shown in FIG. 3, sections of titanium thin films 65 (corresponding to the metal thin films 12 shown in FIG. 3(C)) of a square, rectangular or circular shape are arranged in a lattice on a silicon baseplate 64. Further, on the surface of the silicon baseplate 64 including the titanium thin films 65, a gold thin film 63 with approximately the same thickness as the titanium thin film is formed. The particles 3 are fixed on a region where the gold deposition film 63 and the titanium thin films 65 are not overlapped to define a plurality of sections separately arranged from each other.

By the method as described in the first embodiment, DNA probes are attached to the surface of the particles 3. In this case, the particles of the types for analysis are prepared by the same procedure as in the first embodiment. The particles are prepared in a suspension solution added with carbodiimide, and the suspension solution containing particles is poured down such that the region where the gold deposition film 63 and the titanium thin film 63 are not overlapped.

In this case, the suspension solution is poured down such that the suspension solution does not spread to a region adjacent to the region where titanium and gold are not overlapped. The solution may be poured manually with a small pipette, or the suspension solution of the particles may be spotted to each section using a commercially available micro-array manufacturing system as explained in the first embodiment.

When the spotting is completed, washing is performed by running water, and a micro-array is completed where the particles 3 attached with different types of DNA probes are fixed in each section.

A baseplate 61 is designed to cover where the particles are fixed, and the baseplate is placed in parallel with the side having the particles on the baseplate. The distance between the metal baseplate 61 and the gold deposition film 63 where the particles are fixed to is 0.1–1 mm. Into the gap between the positive pole metal baseplate 61 and the gold deposition film 63 where the particles are fixed, a hybridization reaction solution 66 containing the specimen labeled with fluorescent dye, such as Cy3 or Cy5, is filled by the procedure as described in the first embodiment such that the metal baseplate 61 is set to be the positive pole, and the gold deposition film 63 is set to be the negative pole. Then, a DC electric field is applied to the reaction solution 66 while maintaining the temperature at 65° C. so as to carry out a hybridization reaction. Then, the baseplate of the biochemical sensor is washed, and the DNA reacted with the DNA probes is detected.

To carefully observe the process of hybridization, a mesh-like metal wire is used as the electrode (the positive pole) instead of the metal baseplate 61.

The DNA hybridized with the DNA probes is detected with a microarray scanner by the same procedure as described in the second embodiment.

In the above embodiments, single-stranded DNAs are the substance of interest, and the particles attached with DNA probes on the surface are fixed in each section of the biochemical sensor. When antibody, antigen, receptor, ligand or enzyme is the substance of interest, a corresponding antigen, antibody, ligand, receptor or substrate should be attached to the surface of the particles as biological molecules (probes), and these should be fixed in each section of the biochemical sensor.

Therefore, by changing the type of probe for detecting biological substances (biochemical substances) to be attached to each section of the biochemical sensor, a biochemical testing system is obtained, which can detect various types of biochemical substances using the biochemical sensor of the present invention.

4th Embodiment

Description is given below on a method to market the biochemical sensors of the present invention. The biochemical sensors of the present invention as explained in the above embodiments can be marketed as follows. The biochemical sensors of the present invention comprise a plurality of particles attached with approximately the same number of probes each selectively bonding with the substance of interest in the specimen are caught on the surface, and a planar baseplate where a plurality of sections separately arranged from each other are provided. (1) Each biochemical sensor where the particles are fixed in each section of the biochemical sensor is marketed together with an electronic medium where data of number of the particles fixed per unit area in each section are stored. (2) Each biochemical sensor having approximately the same number of particles per unit area in each section of the biochemical sensor is marketed together with an electronic medium where the data of the number of the particles fixed per unit area in each section are stored. (3) Each biochemical sensor where one layer of a plurality of particles is fixed in the section of each biochemical sensor is marketed together with an electronic medium where the data of the number of the particles fixed per unit area in each section are stored.

The shape and size of each section of the biochemical sensor are also stored in the electronic medium. Further, the average number of molecules (such as DNA probes) for detecting biological substances (biochemical substances) attached to the particles is also stored in the electronic medium, and the particles are fixed in each section of the biochemical sensor. Average value of the number of molecules (the probes) for detecting biological substances (biochemical substances) attached to the particles may be obtained in advance as explained in the first and the second embodiments.

An inexpensive and commonly used floppy disk may be used as the electronic medium, and a biochemical sensor with floppy disk are marketed together.

The average number of molecules (the probes) for detecting the particles fixed in each section of the biochemical sensor is stored in the electronic medium, and each biochemical sensor is marketed with quality assurance. Thus, prior to detecting the substance of interest by reacting with the probes, the user first obtains the number of particles fixed in each section (the value stored in the electronic medium or measured by the user), and the user can obtain average value of the number of molecules (the probes) attached to the particles. Therefore, a biochemical sensor for detecting the substance of interest with high accuracy is provided.

In the prior art, no method is provided for determining the number of DNA probes dropped off from the DNA chip when the DNA probes are bonded with the substance of interest to the DNA chip. Also, no method is provided for determining the degree of the uniformity of DNA probes formed or fixed in each section on the baseplate so as to evaluate the quality of each DNA chip. As a result, in conducting analysis with the DNA chip, there is a serious problem that the quantity of the substance of interest is not accurately reflected in the signal intensity detected from each section of the DNA chip. According to the marketing procedure of the biochemical sensor of the present invention, these problems in the prior art can be solved.

The present invention provides a method for manufacturing a biochemical sensor, comprising the steps of: preparing a plurality of particles attached with approximately the same number of probes each selectively bonding with a substance of interest in a specimen, the probes being attached to the surface of the particles, and said particles being prepared in different containers for each type of the probes; fixing the plurality of particles attached with the probes of different types to each section of the biochemical sensor having a plurality of sections arranged separately from each other on a planar baseplate so that the number of said particles per unit area on each of the sections is approximately the same; and non-destructively determining a number of the particles per unit area fixed in each of the sections by irradiating light to the regions of each of the sections.

The invention also provides a method for manufacturing a biochemical sensor, comprising the steps of: preparing a plurality of particles attached with approximately the same number of probes each selectively bonding with a substance of interest in a specimen, the probes being caught on surface of the particles, and the particles prepared in different containers for each type of the probes; fixing one layer of said plurality of particles where said probes of different types are attached to for each section of the biochemical sensor having a plurality of sections arranged separately from each other on a planar baseplate; and non-destructively determining a number of the particles per unit area fixed in each of the sections by irradiating light to the regions of each of the sections.

The invention provides another method for manufacturing a biochemical sensor, comprising the steps of: preparing a plurality of particles attached with probes selectively bonding with the substance of interest in a specimen, the probes being attached to surface of the particles, and the particles prepared in different containers for each type of the probes; fixing the plurality of particles where the probes of different types are attached to each of the sections of the biochemical sensor having a plurality of section arranged separately from each other in a region where a gold deposition film and a metal deposition film are not overlapped or in a region where the gold deposition film and said metal deposition film are overlapped on each other, the deposition film of a metal other than gold being arranged in a lattice on the surface of a planar baseplate, and the gold deposition film formed on the surface of the baseplate including the region of the metal deposition film; and non-destructively determining a number of the particles per unit area fixed in each of the sections by irradiating light to the regions of each of said sections.

The above-mentioned methods apply the metal deposition film comprising Ti, Cu, or Co, and the plurality of sections are formed on the regions where the gold deposition film and said metal deposition film are not overlapped.

Alternatively, the above-mentioned methods apply the metal deposition film comprising Ag or Cr, and the plurality of sections are formed on the regions where the gold deposition film and the metal deposition film are overlapped.

In the above-mentioned methods, the plurality of particles are fixed in such manner that the number of said particles per unit area in each of the sections is approximately the same, or only one layer of said plurality of particles is fixed on the sections.

In the above-mentioned methods, the particles are polystyrene particles, and they are fixed on the surface of the baseplate by thermal welding.

To market a biochemical sensor of the invention, a marketing method is provided, which comprises the step of marketing said biochemical sensor together with an electronic medium with the data of the number of said particles fixed per unit area in each of said sections, the biochemical sensor comprises a plurality of particles attached with approximately the same number of probes each selectively bonding with a substance of interest in a specimen of said particles, and a planar baseplate with a plurality of sections arranged separately from each other.

Similar, marketing methods are provided for each embodiment of the biochemical sensor of the invention.

According to the present invention, it is possible to provide a biochemical sensor simple and easy to use and capable to detect at high sensitivity as to whether the substance of interest is present or not in a large number of specimens. The invention also provides a biochemical testing system using the biochemical sensor.

The foregoing invention has been described in terms of preferred embodiments. However, those skilled, in the art will recognize that many variations of such embodiments exist. Such variations are intended to be within the scope of the present invention and the appended claims.

What is claimed is:

1. A chemical sensor comprising:
    a planer baseplate;
    a deposition film of a non-gold metal arranged in a lattice on the baseplate;
    a gold deposition film formed over the deposition film of a non-gold metal formed on the baseplate; and
    a plurality of particles attached to the gold deposition film on any one of a first region where the deposition film of a non-gold metal is formed thereunder and a second region where the deposition film of a non-gold metal is not formed thereunder, wherein biochemical probes are immobilized to the particles.

2. The chemical sensor according to claim 1, wherein said plurality of particles makes one layer.

3. The chemical sensor according to claim 1, wherein the deposition film of a non-gold metal is one of Ti, Cu, and Co, and said plurality of particles formed on the gold deposition film of the second region.

4. The chemical sensor according to claim 1, wherein the deposition film of a non-gold metal is one of Ag and Cr, and said plurality of particles formed on the gold deposition film of the first region.

5. The chemical sensor according to claim 1, wherein regions where the plurality of particles are formed make into sections, one layer of said plurality of particles is fixed in each of said sections.

6. The chemical sensors according to claim 1, wherein regions where the plurality of particles are formed make into sections, and different types of biochemical probes are immobilized to the particles in each of said sections.

7. A biochemical testing system using the biochemical sensor according to claim 1.

8. The chemical sensor according to claim 1, wherein the particles are made of glass, silicon, or polymer materials.

9. The chemical sensor according to claim 1, wherein a dimension of the particles is limited by a sensitivity of equipment for testing the particles and a desired number of the probes to be attached to each of the particles.

* * * * *